United States Patent [19]

Ligon

[11] Patent Number: 4,470,929

[45] Date of Patent: Sep. 11, 1984

[54] CONDENSATION OF SUBSTITUTED PHENYLACETONITRILES WITH DICARBOXYLIC ANHYDRIDES

[75] Inventor: Robert C. Ligon, Raleigh, N.C.

[73] Assignee: Union Carbide Corporation, Danbury, Conn.

[21] Appl. No.: 480,733

[22] Filed: Mar. 31, 1983

[51] Int. Cl.³ .......................................... C07C 121/76
[52] U.S. Cl. ............................................... 260/465 D
[58] Field of Search .................................. 260/465 D

[56] References Cited

U.S. PATENT DOCUMENTS 4,175,135 11/1979 Haines ................................ 424/311
4,256,657 3/1981 Wheeler .......................... 260/465 D
4,422,870 12/1983 Wheeler ............................... 71/106

OTHER PUBLICATIONS

V. Oskaja et al., C.A., 56, 10029, (1962).
P. Hrneiar, C.A., 60, 4053, (1964).
Hannout et al., J. fus Prakt Chem., 316, 463, (1974).

Primary Examiner—Dolph H. Torrence
Attorney, Agent, or Firm—J. A. Shedden

[57] ABSTRACT

This invention relates to the stoichiometric condensation of substituted phenylacetonitriles with dibasic carboxylic anhydrides. The resulting cyano-keto-acids are obtained in good yield and can be used to prepare biologically active 2-aryl-1,3-cyclohexanediones without elaborate purification.

10 Claims, No Drawings

CONDENSATION OF SUBSTITUTED PHENYLACETONITRILES WITH DICARBOXYLIC ANHYDRIDES

FIELD OF THE INVENTION

This invention relates to a novel method of preparing cyano-keto-acids from the stoichiometric condensation of substituted phenylacetonitriles with dibasic carboxylic anhydrides.

BACKGROUND OF THE INVENTION

Certain 2-aryl-1,3-cyclohexanediones and their esters are known to be extremely active, biological compounds. U.S. Pat. Nos. 4,175,135 and 4,256,657 and copending application U.S. Ser. No. 781,781 filed Mar. 28, 1977, all of which are herein incorporated by reference, teach the usefulness of these compounds as herbicidal and miticidal agents and as agents for orally controlling acarina ectoparasites on warm-blooded animals.

Cyano-keto-acids, such as the 6-aryl-6-cyano-5-ketohexanoic acids and/or their esters are important intermediates in the manufacture of the afore-described 2-aryl-1,3-cyclohexanediones.

U.S. Pat. No. 4,256,657 teaches that the coupling of ring-substituted phenylacetonitriles with alkyl-substituted glutaric acid derivatives in a basic reaction medium will result in esters of the cyano-keto-acids described above, e.g. Example XVI of said patent. However, a significant disadvantage to this process is the large molar excess (50 to 200%) of glutaric acid derivative required to suppress reaction of a second molecule of ring-substituted phenylacetonitrile with the desired product.

SUMMARY OF THE INVENTION

In accordance with the present invention, it has been discovered that good yields of cyano-keto-acids can be realized by the stoichiometric coupling of ring-substituted phenylacetonitriles with substituted glutaric anhydride. Furthermore, the resulting substituted hexanoic acid may be incorporated directly into the prior art process of U.S. Pat. No. 4,175,135 for the production of 2-aryl-1,3-cycylohexanediones.

DETAILED DESCRIPTION OF THE INVENTION

The invention relates to the discovery that ring-substituted phenylacetonitriles can be stoichometrically coupled with substituted glutaric anhydrides to produce cyano-keto-hexanoic acids in good yields.

Specifically, the invention relates to the discovery that compounds of the formula

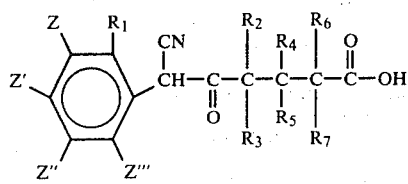

can be prepared in good yield by reacting a phenylacetonitrile of the formula:

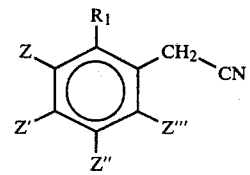

wherein Z, Z', Z'' and Z''' are individually hydrogen, nitro, polyhaloalkyl, halogen, cyano, alkyl, alkoxy, alkylthio, alkylsulfinyl, alkylsulfonyl, alkanoyl, amido, amino, or haloalkyl; and $R_1$ is alkyl, halogen, polyhaloalkyl, or haloalkyl;

with a stoichiometric amount of a compound of the formula:

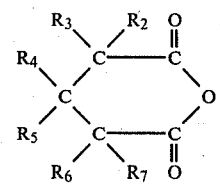

wherein $R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl, or dialkylamino substituents or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;

with the proviso that $R_1$, $R_2$, $R_3$, $R_4$, $R_5$, $R_6$, $R_7$, Z, Z', Z'' and Z''' substituents individually may not include more than ten aliphatic carbon atoms; in the presence of a base and a non-protic solvent at a temperature of from about 60° C. to about 150° C.

Although the temperature and pressure of the process are not critical, it is preferred to operate at from about 100° C. to about 140° C. and most preferably from about 120° C. to about 135° C. at atmospheric pressure.

Preferred substituents in the reactions of this invention, primarily because of the high miticidal effects realized in the 2-substituted-1,3-cyclohexanediones derived from the intermediates of this invention, are the following:

Z, Z', Z'' and Z''' are individually hydrogen, alkyl, cyano, alkoxy, halogen, or trihalomethyl;

$R_1$ is alkyl or halogen; and $R_2$, $R_3$, $R_4$, $R_5$, $R_6$ and $R_7$ are individually hydrogen or alkyl.

The most preferred substituents are the following:

Z, Z', Z'' and Z''' are individually hydrogen, methyl, methoxy, cyano, or halogen;

$R_1$ is methyl or halogen; and $R_2$, $R_3$, $R_4$, $R_5$, $R_6$ and $R_7$ are individually hydrogen, methyl or ethyl.

Illustrative of the strong bases which are useful in the reactions of this invention are the metal alcoxides, alkali metal amides, alkali metal hydrides or mixtures of these bases.

The preferred base is sodium ethoxide.

It is also preferred that at least two equivalents of base be present during the reaction.

Illustrative of the non-protic solvents which are useful in this invention are the aromatic hydrocarbons, cyclic and acylic ethers, dimethyl sulfoxide, dimethylformamide, and sulfolane. The preferred non-protic solvents are dimethoxyethane, tetrahydrofuran, n-butyl ether, dioxane and xylene.

The following examples are set forth for purposes of illustration so that those skilled in the art may better understand the invention, and it should be understood that they are not to be construed as limiting this invention in any manner.

EXAMPLE I

Preparation of 6-cyano-3,3-dimethyl-5-keto-6-(2-methylphenyl)hexanoic acid (METHOD I)

To a suspension of a sodium amide-sodium t-butoxide complex, prepared by adding 9.5 g of t-butanol in 25 ml of dry tetrahydrofuran to 10 g of sodium amide in 50 ml dry tetrahydrofuran and purging with $N_2$ for 15 minutes, was added at 0° C. a solution of 13.1 g 2-methylphenylacetonitrile in 25 ml tetrahydrofuran. The solution was held at 0° C. for 30 minutes while flushing the reaction system with $N_2$ to remove the ammonia liberated. A solution of 14.2 g 3,3-dimethylglutaric anhydride dissolved in 75 ml tetrahydrofuran was added as rapidly as possible and the solution heated to reflux for 5 hours. The reaction mixture was cooled to 40° C. and quenched with 150 ml. water. The organic layer was separated, diluted with 75 ml ethyl ether, and extracted with 100 ml water. The combined aqueous layers were extracted once with 75 ml ethyl ether, then acidified to pH 2 with concentrated hydrochloric acid. The aqueous solution was extracted three times with 75 ml of methylene chloride and the combined methylene chloride extracts dried over magnesium sulfate. Stripping the solvent at reduced pressure produced a residue containing 16.42 g of 6-cyano-3,3-dimethyl-5-keto-6-(2-methylphenyl)hexanoic acid.

EXAMPLE II

Preparation of 6-cyano-3,3-dimethyl-5-keto-6-(2-methylphenyl)hexanoic acid (METHOD II)

To a solution of sodium ethoxide in xylenes, prepared by adding 25 ml ethanol to 4.6 g of sodium metal suspended in 100 ml xylenes, refluxing 1 hr. then distilling out the excess ethanol, was added a solution of 13.1 g 2-methylphenylacetonitrile and 14.2 g 3,3-dimethylglutaric anhydride dissolved in 25 ml hot xylenes. The resulting slurry was held at reflux for 20 hrs with continuous removal of the by-product ethanol by distillation. The mixture was then cooled to ambient temperature and 100 ml cold water added. After stirring for 5 minutes the layers were separated and the organic layer extracted with an additional 50 ml of water. The combined aqueous layers were acidified to pH 2 with concentrated sulfuric acid and extracted twice with 75 ml ethyl ether. The combined ether extracts were dried over magnesium sulfate and the solvent removed under vacuum to produce a yellow gummy residue containing 17.75 g 6-cyano-3,3-dimethyl-5-keto-6-(2-methylphenyl)hexanoic acid.

I claim:

1. A method of preparing a compound of the formula:

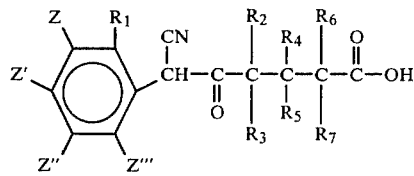

which comprises:
reacting a compound of the formula

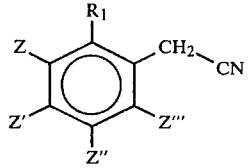

wherein Z, Z', Z" and Z''' are individually hydrogen, nitro, polyhaloalkyl, halogen, cyano, alkyl, alkoxy, alkylthio, alkylsulfinyl, alkylsulfonyl, alkanoyl, amido, amino, or halo-alkyl; and $R_1$ is alkyl, halogen, polyhaloalkyl, or haloalkyl;
with a compound of the formula:

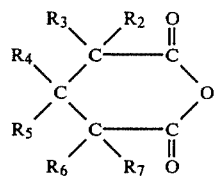

wherein $R_2$, $R_3$, $R_4$, $R_5$, $R_6$ and $R_7$ are individually hydrogen or either substituted or unsubstituted alkyl or phenyl wherein the permissible substituents are one or more alkyl, cyano, halogen, nitro, alkoxy, alkylthio, alkylsulfinyl, alkylsulfonyl, or dialkylamino substituents or any two $R_2$, $R_3$, $R_4$, $R_5$, $R_6$ or $R_7$ substituents together may form an alkylene or alkenylene chain having from 2 to 20 carbon atoms completing a 3, 4, 5, 6 or 7 membered ring structure;
with the proviso that $R_1$, $R_2$, $R_3$, $R_4$, $R_5$, $R_6$, $R_7$, Z, Z', Z" and Z''' substituents individually may not include more than ten aliphatic carbon atoms; in the presence of a base and a non-protic solvent.

2. The method according to claim 1 wherein
Z, Z', and Z''' are individualy hydrogen, alkyl, cyano, alkoxy, halogen, or trihalomethyl;
$R_1$ is alkyl or halogen; and $R_2$, $R_3$, $R_4$, $R_5$, $R_6$ and $R_7$ are individually hydrogen or alkyl.

3. The method according to claim 1 wherein Z, Z', Z" and Z''' are individually hydrogen, methyl, methoxy, cyano, or halogen;
$R_1$ is methyl or halogen; and $R_2$, $R_3$, $R_4$, $R_5$, $R_6$ and $R_7$ are individually hydrogen, methyl or ethyl.

4. The method according to claim 1 wherein said base comprises a metal alkoxide, alkali metal amide, alkali metal hydride or mixtures thereof.

5. The method according to claim 4 wherein said base comprises sodium ethoxide.

6. The method according to claim 4 wherein said base comprises sodium amide.

7. The method according to claim 1 wherein said non-protic solvent is selected from the group consisting of aromatic hydrocarbons, cyclic ethers, acyclic ethers, dimethyl sulfoxide, dimethylformamide, and sulfolane.

8. The method according to claim 7 wherein said non-protic solvent is selected from the group consisting of dimethoxyethane, tetrahydrofuran, n-butyl ether, dioxane and xylene.

9. The method according to claim 1 wherein the reaction temperature is from about 60° C. to about 150° C. at atmospheric pressure.

10. The method according to claim 9 wherein the reaction temperature is from about 100° C. to 140° C.

* * * * *